(12) United States Patent
Liang et al.

(10) Patent No.: US 11,397,231 B2
(45) Date of Patent: Jul. 26, 2022

(54) MAGNETIC-RESONANCE IMAGING METHOD, APPARATUS AND SYSTEM, AND STORAGE MEDIUM

(71) Applicant: SHENZHEN INSTITUTES OF ADVANCED TECHNOLOGY, Guangdong (CN)

(72) Inventors: Dong Liang, Guangdong (CN); Jing Cheng, Guangdong (CN); Haifeng Wang, Guangdong (CN); Hairong Zheng, Guangdong (CN); Xin Liu, Guangdong (CN)

(73) Assignee: Shenzhen Institutes of Advanced Technology, Guangdong (CN)

( * ) Notice: Subject to any disclaimer, the term of this patent is extended or adjusted under 35 U.S.C. 154(b) by 175 days.

(21) Appl. No.: 16/624,478

(22) PCT Filed: Sep. 17, 2019

(86) PCT No.: PCT/CN2019/106218
§ 371 (c)(1),
(2) Date: Dec. 19, 2019

(87) PCT Pub. No.: WO2020/215597
PCT Pub. Date: Oct. 29, 2020

(65) Prior Publication Data
US 2021/0333344 A1    Oct. 28, 2021

(30) Foreign Application Priority Data
Apr. 24, 2019    (CN) .................. 201910333593.6

(51) Int. Cl.
*G01R 33/48*    (2006.01)
*G01R 33/56*    (2006.01)
*A61B 5/055*    (2006.01)

(52) U.S. Cl.
CPC ..... *G01R 33/4818* (2013.01); *G01R 33/5608* (2013.01); *A61B 5/055* (2013.01)

(58) Field of Classification Search
CPC .. G01R 33/4818; G01R 33/5608; A61B 5/055
See application file for complete search history.

(56) References Cited

U.S. PATENT DOCUMENTS

| 2013/0073489 A1* | 3/2013 | Qin ........................ G06N 20/10 |
| | | 706/12 |
| 2018/0285695 A1* | 10/2018 | Guo ....................... G06T 7/0012 |
| 2019/0172230 A1* | 6/2019 | Mailhe ................... G06N 3/084 |

FOREIGN PATENT DOCUMENTS

| CN | 103646410 A | 3/2014 |
| CN | 104574456 A | 4/2015 |

(Continued)

OTHER PUBLICATIONS

Machine Translation of CN 106373167 A obtained on Aug. 12, 2021 (Year: 2017).*

(Continued)

*Primary Examiner* — Gregory H Curran
(74) *Attorney, Agent, or Firm* — Duane Morris LLP (57) ABSTRACT

Disclosed are a magnetic-resonance imaging method, apparatus and system, and a storage medium. The method includes acquiring an initial model of magnetic-resonance imaging and establishing an initial imaging model according to an iterative algorithm used for solving the initial model, where the iterative algorithm includes at least one of an undetermined parameter, an undetermined solving operator or an undetermined structural relationship; training the initial imaging model on the basis of sample data to generate a magnetic-resonance imaging model, where training of the initial imaging model is used for learning the at least one of the undetermined parameter, the undetermined solving operator or the undetermined structural relationship in the (Continued)

iterative algorithm; and acquiring under-sampled K-space data to be processed, inputting the under-sampled K-space data into the magnetic-resonance imaging model, and generating a magnetic-resonance image.

11 Claims, 6 Drawing Sheets

(56) References Cited

FOREIGN PATENT DOCUMENTS

| | | |
|---|---|---|
| CN | 106373167 A | 2/2017 |
| CN | 106780372 A | 5/2017 |
| CN | 107064845 A | 8/2017 |
| CN | 109325985 A | 2/2019 |
| CN | 109410289 A | 3/2019 |
| WO | 2015164825 A1 | 10/2015 |

OTHER PUBLICATIONS

International Search Report issued in connection with corresponding International Patent Application No. PCT/CN2019/106218, dated Feb. 6, 2020, 8 pages.

* cited by examiner

FIG. 1

| Acquire an original model of magnetic-resonance imaging and establish an initial imaging model according to an iterative algorithm used for solving the original model, where the iterative algorithm includes at least one of an undetermined parameter, an undetermined solving operator or an undetermined structural relationship | ~ S110 |

↓

| Train initial imaging model on the basis of sample data and generate a magnetic-resonance imaging model, where training of the initial imaging model is used for learning the at least one of the undetermined parameter, the undetermined solving operator or the undetermined structural relationship in the iterative algorithm | ~ S120 |

↓

| Acquire under-sampled K-space data to be processed, input the under-sampled K-space data into the magnetic-resonance imaging model, and generate a magnetic-resonance image | ~ S130 |

# MAGNETIC-RESONANCE IMAGING METHOD, APPARATUS AND SYSTEM, AND STORAGE MEDIUM

CROSS REFERENCE TO RELATED APPLICATIONS

This application is a National Stage Application, filed under 35 U.S.C. 371, of International Patent Application No. PCT/CN2019/106218, filed on Sep. 17, 2019, which claims priority to a Chinese patent application No. 201910333593.6 filed on Apr. 24, 2019, disclosure of which are incorporated herein by reference in their entireties.

TECHNICAL FIELD

Embodiments of the present application relate to deep learning techniques, for example, to a magnetic-resonance imaging method, apparatus and system, and a storage medium.

BACKGROUND

Magnetic resonance uses static magnetic fields and radio-frequency magnetic fields to image human tissue. The magnetic resonance not only provides rich tissue contrast, but also is harmless to human body, thus becoming a powerful tool for medical clinical diagnosis. However, slow imaging speed has been a big bottleneck for the rapid development of magnetic-resonance imaging.

In fast imaging, common techniques are parallel imaging and compressed sensing. The parallel imaging uses correlation between multi-channel coils to accelerate acquisition, and the compressed sensing uses prior information about sparsity of an imaged subject to reduce K-space sampled points. However, due to conditions such as hardware and the like, the parallel imaging acceleration multiple is limited, and a noise-amplification phenomenon of an image will occur along with an increase of the acceleration multiple; and the compressed sensing technique has very long reconstruction time due to adoption of iteration reconstruction, and sparse transformation and reconstruction parameters are difficult to select.

SUMMARY

The present application provides a magnetic-resonance imaging method, apparatus and system, and a storage medium to improve the quality of a magnetic-resonance image.

An embodiment of the present application provides a magnetic-resonance imaging method. The method includes the steps described below.

An original model for magnetic-resonance imaging is acquired and an initial imaging model is established according to an iterative algorithm used for solving the original model. The iterative algorithm includes at least one of an undetermined parameter, an undetermined solving operator or an undetermined structural relationship.

The initial imaging model is trained on the basis of sample data to generate a magnetic-resonance imaging model. Training of the initial imaging model is used for learning the at least one of the undetermined parameter, the undetermined solving operator or the undetermined structural relationship in the iterative algorithm.

Under-sampled K-space data to be processed is acquired, the under-sampled K-space data is input into the magnetic-resonance imaging model, and a magnetic-resonance image is generated.

An embodiment of the present application further provides a magnetic-resonance imaging apparatus. The apparatus includes an initial-imaging-model establishing module, a model-training module and a magnetic-resonance imaging module.

The initial-imaging-model establishing module is configured to acquire an original model for magnetic-resonance imaging and establish an initial imaging model according to an iterative algorithm used for solving the original model. The iterative algorithm includes at least one of an undetermined parameter, an undetermined solving operator or an undetermined structural relationship.

The model-training module is configured to train the initial imaging model on the basis of sample data to generate a magnetic-resonance imaging model. Training of the initial imaging model is used for learning the at least one of the undetermined parameter, the undetermined solving operator or the undetermined structural relationship in the iterative algorithm.

The magnetic-resonance imaging module is configured to acquire under-sampled K-space data to be processed, input the under-sampled K-space data into the magnetic-resonance imaging model, and generate a magnetic-resonance image.

An embodiment of the present application further provides a computer-readable storage medium storing a computer program. When the computer program is executed by a processor, the magnetic-resonance imaging method provided by any embodiment of the present application is performed.

An embodiment of the present application further provides a magnetic-resonance imaging system. The system includes a magnetic-resonance device and a computer device. The computer device includes a memory, one or more processors and a computer program stored in the memory and executable on the processor. When the processor executes the computer program, the processor performs the magnetic-resonance imaging method provided by any embodiment of the present application.

DETAILED DESCRIPTION

The present application will be described below in conjunction with drawings and embodiments. The embodiments described below are intended to explain but not to limit the present application. For ease of description, only part, not all, of structures related to the present application are illustrated in the drawings.

A magnetic-resonance imaging system generally includes a magnet having a bore, a transmit coil for transmitting radio-frequency signals and a receive coil for receiving magnetic-resonance signals, a gradient coil for spatially positioning the magnetic-resonance signals, a pulse generator for generating a scanning sequence, and a control system. An operator (clinician) controls a console connected to the control system to make the magnetic-resonance imaging system operate. The console may include a keyboard or other input devices, a control panel and a display so that commands can be inputted and generated images can be displayed.

Figure 1:
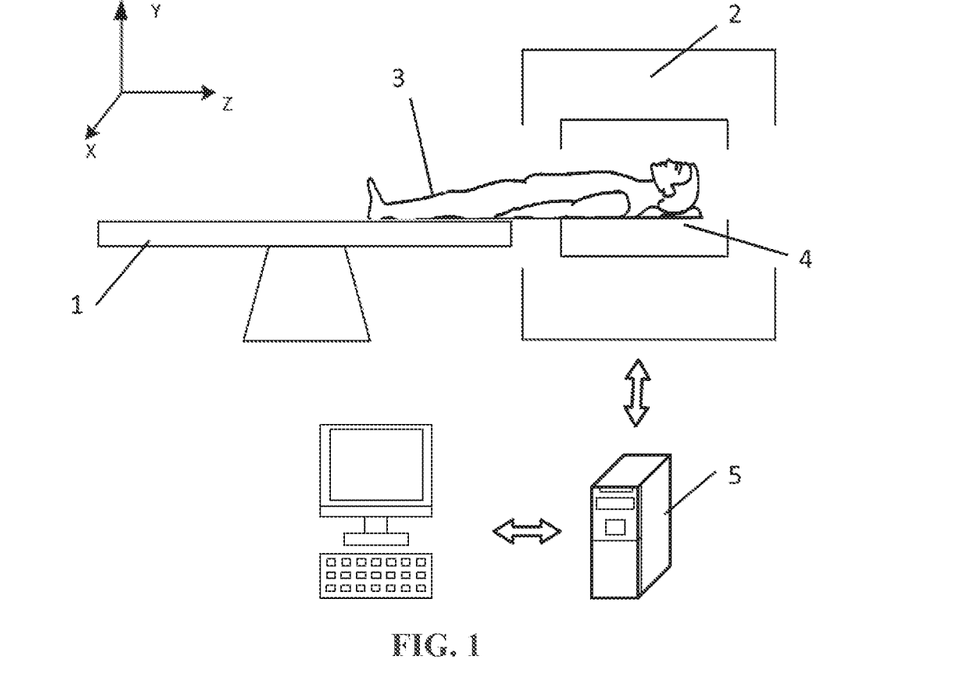
FIG. 1 is a structural diagram of a magnetic-resonance imaging system of the prior art.

FIG. 1 is a structural diagram of a magnetic-resonance imaging system of the prior art. In a magnetic-resonance examination, a clinician first places a detection subject 3 onto a scanning bed 1 and places, on the body of the detection subject 3, local coils for receiving magnetic-resonance signals, and then the clinician operates a console connected to a control system 5 to control the scanning bed 1 to move into a bore formed from a magnet 2. After the magnetic-resonance imaging system monitors an instruction of moving the scanning bed 1 sent by the clinician, the magnetic-resonance imaging system monitors the moving range of the scanning bed 1 through the control system 5. When the scanning bed 1 enters the edge of a scanning imaging area 4, the control system 5 controls a pulse sequence generator to generate a corresponding sequence for scanning. The sequence may control and stimulate generation of a radio-frequency pulse, and the radio frequency pulse may stimulate generation of a processing nuclear spin in the body area of the detection subject 3. During the movement of the scanning bed 1, the gradient magnetic field generated by gradient coils may perform phase encoding, frequency encoding or layer encoding on the precession nuclear spin, and the receiving coils placed on the body of the subject 3 are movable with the scanning bed 1 in the inner space of the magnet space. The receiving coils at different positions are in an open state or a closed state under the control of the control system 5 so as to receive corresponding magnetic-resonance signals.

Embodiment One

Figure 2:
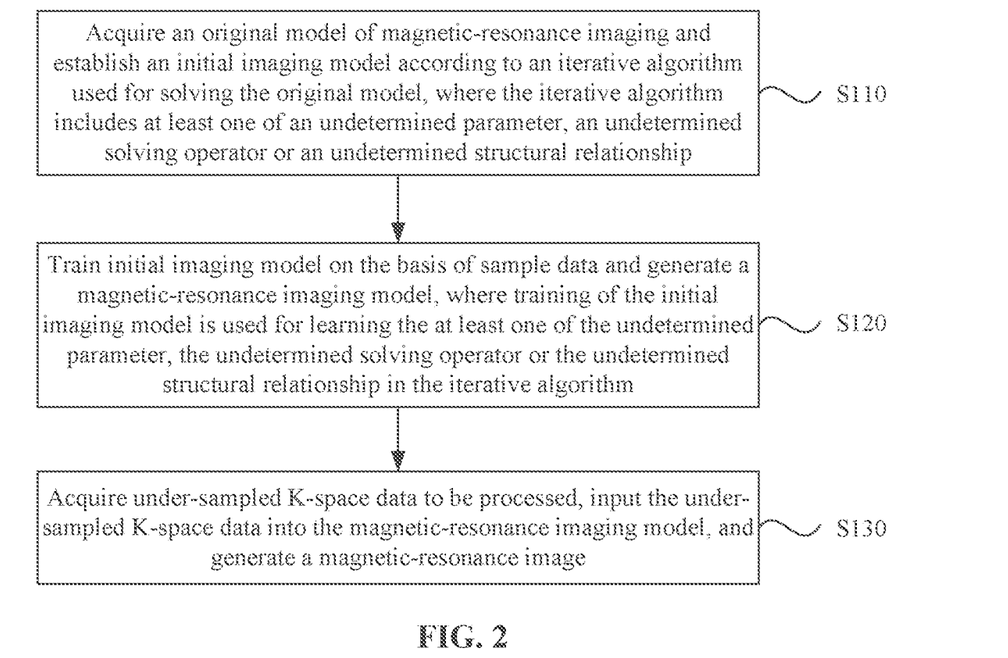
FIG. 2 is a flowchart of a magnetic-resonance imaging method according to embodiment one of the present application.

FIG. 2 is a flowchart of a magnetic-resonance imaging method according to embodiment one of the present application. This embodiment is applicable to magnetic-resonance imaging on the basis of a neural network, and the method may be performed by a magnetic-resonance imaging apparatus provided by an embodiment of the present application. The magnetic-resonance imaging method includes steps S110 to S130.

In S110, an original model for magnetic-resonance imaging is acquired and an initial imaging model is established according to an iterative algorithm used for solving the original model. The iterative algorithm includes at least one of an undetermined parameter, an undetermined solving operator or an undetermined structural relationship.

In S120, the initial imaging model is trained on the basis of sample data to generate a magnetic-resonance imaging model. Training of the initial imaging model is used for learning the at least one of the undetermined parameter, the undetermined solving operator or the undetermined structural relationship in the iterative algorithm.

In S130, under-sampled K-space data to be processed is acquired, the under-sampled K-space data is input into the magnetic-resonance imaging model, and a magnetic-resonance image is generated.

In an embodiment, the iterative algorithm may be any one of a basic dual algorithm, an alternating direction multiplier algorithm or an iterative threshold shrinkage algorithm, and the initial imaging model is established according to a selected iterative algorithm. The initial imaging model may include a preset number of iteration modules. A connection relationship between multiple iteration modules is determined according to the iterative algorithm, and the preset number of iteration modules is connected to form the initial imaging model. Each iteration module may be a calculation module including an undetermined factor or may be a network module including multiple network layers. The iterative algorithm may include any one undetermined factor of the undetermined parameter, the undetermined solving operator or the undetermined structural relationship or may include two or three undetermined factors of the undetermined parameter, the undetermined solving operator and the undetermined structural relationship. Accordingly, the initial imaging model includes the undetermined factor corresponding to the iterative algorithm. Exemplarily, if the initial imaging model is a network model, then the undetermined factor is replaced on the basis of an undetermined network parameter of the network model. In an embodiment, the undetermined parameter may be a parameter used for processing input information in the iterative algorithm; the undetermined structural relationship may be a calculation relationship between multiple pieces of input information or between multiple pieces of input information processed through the undetermined parameter in the iterative algorithm, for example, the undetermined structural relationship may be addition, subtraction, multiplication or division; and the undetermined solving operator may be a calculation function performed on the input information or the input information processed through the undetermined parameter in the iterative algorithm.

In this embodiment, the step in which the initial imaging model is established according to the selected iterative algorithm and the initial imaging model is trained on the basis of the sample data in a sample set may include: the sample data is input into the initial imaging model to obtain an output magnetic-resonance image of the initial imaging model, a loss function is determined according to the output magnetic-resonance image and a standard magnetic-resonance image generated through full-sampled K-space data corresponding to the sample data, a to-be-learned parameter of the initial imaging model (for example, the network parameter of the network model or the undetermined parameter of the calculation model, etc.) is adjusted according to the loss function to generate the magnetic-resonance imaging model. In an embodiment, the sample data may be under-sampled K-space data acquired through magnetic-resonance detection of multiple detection targets. An iterative process of the input sample data is performed sequentially through preset layers of iteration models of the initial imaging model to be trained so as to generate the output magnetic-resonance image of the initial imaging model. The loss function is determined according to the output magnetic-resonance image and the standard magnetic-resonance image generated through the full-sampled K-space data corresponding to the sample data, and the to-be-learned parameter of the initial imaging model is reversely adjusted according to the loss function. Next sample data is processed on the basis of the adjusted initial imaging model. The above training process is circularly performed until a loss value obtained according to the loss function is smaller than an error value and the training of the magnetic-resonance imaging model is determined to be completed. In an embodiment, the loss function loss is determined according to the following formula: loss=$\|\hat{x}-x_{ref}\|_2^2$, where $\hat{x}$ denotes the output magnetic-resonance image of the initial imaging model and $x_{ref}$ denotes the standard magnetic-resonance image generated through the full-sampled K-space data corresponding to the sample data.

In this embodiment, initial imaging models established on the basis of iterative algorithms including different undetermined factors may be trained on the basis of different sample data, for example, different amounts of sample data. Exemplarily, the greater the number of undetermined factors included in the iterative algorithm is, the greater the amount of sample data used for training the initial imaging model established on the basis in the iterative algorithm is.

In the technical solution provided by this embodiment, the initial imaging model is established according to the iterative algorithm including the at least one of the undetermined parameter, the undetermined solving operator or the undetermined structure relationship, and the initial imaging model is trained to learn the undetermined factors in the iterative algorithm, and the learnt undetermined factors are used to replace a fixed solving operator, a fixed parameter and a fixed structural relationship in the related art. In this manner, freedom degree of the magnetic-resonance imaging model is improved and the quality of a reconstructed magnetic-resonance image generated on the basis of the magnetic-resonance imaging model obtained through learning is improved compared with the traditional mode.

In an embodiment, the step in which the initial imaging model is trained on the basis of the sample data and the magnetic-resonance imaging model is generated includes that: first sample data in the sample set, an initial parameter, and an initial image are processed on the basis of the undetermined parameter and a preset structural relationship, and first input information is obtained; and the initial imaging model is iteratively trained on the basis of the first input information, the undetermined parameter is learned, and a first magnetic-resonance imaging model used for the magnetic-resonance imaging is generated. In this embodiment, the initial imaging model includes a preset number of iteration modules, the preset number of iteration modules are sequentially connected and used for iteratively processing the first input information, and each iteration module includes a preset solving operator. In this embodiment, the initial parameter may be 0, and pixel data of the initial image may be 0. In this embodiment, the undetermined parameter is learned through the initial imaging model, and the each iteration module of the initial imaging model includes the fixed structural relationship and the fixed solving operator. The initial imaging model is trained through the above training method, and the first magnetic-resonance imaging model which may be used for the magnetic-resonance imaging is obtained. On the basis of a traditional iterative algorithm, the undetermined parameter determined by the above method through learning replaces the fixed parameter determined on the basis of empirical values, thereby improving applicability of the model. Meanwhile, only the undetermined parameter needs to be learned in the above training method, so the amount of required training sample data is small and the method is applicable to the case of a small amount of sample data.

In some embodiments, the structure of the initial imaging model may be adjusted, so that undetermined factors are sequentially increased and the undetermined parameter, the undetermined solving operator and the undetermined structural relationship in the iterative algorithm are sequentially learned, and thereby the magnetic-resonance imaging model with high precision is established. In an embodiment, the initial imaging model including the preset structural relationship, the undetermined parameter and the preset solving operator is established; second sample data in the sample set, the initial parameter and the initial image are processed on the basis of the undetermined parameter and the preset structural relationship, and second input information is obtained; and the initial imaging model is iteratively trained on the basis of the second input information, the undetermined parameter and the network parameter of the initial imaging model are determined, and a second magnetic-resonance imaging model used for the magnetic-resonance imaging is generated. The initial imaging model includes a preset number of iteration sub-network models, the preset number of iteration sub-network models are sequentially connected and used for iteratively processing the second input information, and the network parameter of the initial imaging model is used for replacing the preset solving operator. Through the second sample data, the initial imaging model is trained, the undetermined parameter is learned, and the second magnetic-resonance imaging model is generated. The second magnetic-resonance imaging model may be used for performing step S130 in which the to-be-processed under-sampled K-space data is processed and the magnetic-resonance image is obtained.

In an embodiment, a structural adjustment may be performed on the first magnetic-resonance imaging model, the preset number of iteration modules of the first magnetic-resonance imaging model is replaced on the basis of the preset number of iteration sub-network models, and then the adjusted first magnetic-resonance imaging model is trained by using the above second sample data and the second magnetic-resonance imaging model is obtained. In an embodiment, the training may be performed on the basis of the undetermined parameter obtained from the training of the first magnetic-resonance imaging model, so that the adjusted first magnetic-resonance imaging model can be trained quickly, and training efficiency is improved.

In an embodiment, after the step in which the second magnetic-resonance imaging model used for the magnetic-resonance imaging is generated, the method further includes that: unprocessed third sample data in the sample set, the initial parameter and the initial image are used as third input information, the undetermined structural relationship and the undetermined solving operator are learned, and a third magnetic-resonance imaging model used for the magnetic-resonance imaging is generated. On the basis of the second magnetic-resonance imaging model, the preset structural relationship of the second magnetic-resonance imaging model is replaced based on the undetermined structural relationship, the second magnetic-resonance imaging model is updated, and the updated second magnetic-resonance imaging model is trained based on the third sample data. In the training process, the undetermined structural relationship and the undetermined solving operator are learned (where the solving operator of the second magnetic-resonance imaging model is updated in the training process), and the third magnetic-resonance imaging model is obtained. In this embodiment, the second sample data and the third sample data may be the same or different. In this embodiment, on the basis of the second magnetic-resonance imaging model obtained through the training, the model structure of the second magnetic-resonance imaging model is adjusted, a new undetermined factor is introduced, and a third magnetic-resonance imaging model is obtained after training. The undetermined factors in the iterative algorithm are sequentially learned in a progressive training mode, and this can reduce the number of samples applied in the training process. Meanwhile, the training is performed on the basis of the network parameter of the second magnetic-resonance imaging model, thereby improving training efficiency of the third magnetic-resonance imaging model.

In an embodiment, on the basis of the first magnetic-resonance imaging model, the preset number of iteration modules of the first magnetic-resonance imaging model is replaced based on the preset number of iteration sub-network modules, and the adjusted first magnetic-resonance imaging model includes the undetermined solving operator and the undetermined structural relationship. The adjusted first magnetic-resonance imaging model is trained by using the above third sample data, and the third magnetic-resonance imaging model is obtained.

On the basis of the above embodiment, the original model for the magnetic-resonance imaging includes a sparse transform algorithm. Accordingly, the method further includes that: a sub-network model for executing the sparse transform algorithm is established, where the sub-network model is connected to an output end of the magnetic-resonance imaging model; and the sub-network model is trained on the basis of fourth sample data in the sample set, and a fourth magnetic-resonance imaging model is generated on the basis of the trained sub-network model. In this embodiment, the magnetic-resonance imaging model connected to the sub-network model may be any one of the first magnetic-resonance imaging model, the second magnetic-resonance imaging model or the third magnetic-resonance imaging model.

In some embodiments, the imaging model may be $$\min_x \|F_u x - y\|_2^2 + \lambda \|\Psi x\|_1.$$

In this imaging model, $\lambda$ denotes a canonical parameter, and $\Psi$ denotes a sparse transform. In the traditional magnetic-resonance imaging, a fixed-base sparse transform is adopted. However, the fixed-base sparse transform cannot sparsely represent all information of an image completely. In this embodiment, the sub-network model for executing the sparse transform algorithm is established and connected to the output end of the magnetic-resonance imaging model, so that a new magnetic-resonance imaging model is generated. The sub-network model may be a neural magnetic-resonance imaging model, for example, a convolutional neural network (CNN) model including a preset layers of convolutional layers and activation layers. The convolution kernel of each convolutional layer may be (3×3). The sub-network model may be connected to an output end of the first magnetic-resonance imaging model, the second magnetic-resonance imaging model or the third magnetic-resonance imaging model, so that the new magnetic-resonance imaging model is generated. A sub-network model for the new magnetic-resonance imaging model is trained on the basis of the fourth sample data. In an embodiment, the fourth sample is input into the new magnetic-resonance imaging model and an output magnetic-resonance image is output, a loss function is determined according to the output magnetic-resonance image and a standard magnetic-resonance image generated through full-sampled K-space data corresponding to the fourth sample data, and the network parameter of the network model is adjusted. When the training of the sub-network model is completed, the fourth magnetic-resonance imaging model used for the magnetic-resonance imaging is generated. In this embodiment, the fourth magnetic-resonance imaging model may include a trained sub-network model and the first magnetic-resonance imaging model, may include the trained sub-network model and the second magnetic-resonance imaging model, or may include the trained sub-network model and the third magnetic-resonance imaging model.

In the above embodiment, in the process of training any magnetic-resonance imaging model or sub-network model, a stochastic gradient descent (SGD) algorithm may be adopted to adjust the network parameter of the model.

In an embodiment, in the process of training any magnetic-resonance imaging model or sub-network model, input information of the magnetic-resonance imaging model may be input into the magnetic-resonance imaging model and an output magnetic-resonance image of the magnetic-resonance imaging model is obtained, a loss function is determined according to the output magnetic-resonance image and a standard magnetic-resonance image generated through full-sampled K-space data corresponding to the input information, and a network parameter of the imaging model is adjusted according to the loss function.

In the technical solution provided by this embodiment, the magnetic-resonance imaging model replaces the traditional iterative algorithm, thereby improving the freedom degree of the magnetic-resonance imaging model. Meanwhile, the undetermined factors sequentially replace fixed factors, the magnetic-resonance imaging model is adjusted, and the adjusted magnetic-resonance imaging model is separately trained on the basis of the sample data, so that the magnetic-resonance imaging model used for the magnetic-resonance imaging is obtained. The sample data in different training processes may overlap, thereby reducing the requirement on the amount of sample data. The training is performed on the basis of a previous training result, thereby reducing model training difficulty and improving model training efficiency and imaging precision of the magnetic-resonance imaging model.

A construction mode of the initial imaging model will be introduced by using the basic dual algorithm as an example. Exemplarily, the original model for the magnetic-resonance imaging may be minimization formula (1).

$$\min_x \|F_u x - y\|_2^2 + \lambda R(x) \quad (1)$$

In formula (1), x denotes a magnetic-resonance image to be reconstructed, y denotes under-sampled K-space data obtained through magnetic-resonance scanning, $F_u$ denotes an under-sampled Fourier transform operator, and R(x) denotes a constraint term.

The original model for the magnetic-resonance imaging above may be iteratively solved through the basic dual algorithm. In traditional magnetic-resonance imaging, assuming that $F(Ax) = \|Ax - y\|_2^2$ and $A = F_u$, the original model may be solved through the iterative algorithm described below.

$$\begin{cases} d_{n+1} = prox_\sigma[F^*](d_n + \sigma A p_n) \\ x_{n+1} = prox_\tau[R](x_n - \tau A^* d_{n+1}) \\ p_{n+1} = x_{n+1} + \theta(x_{n+1} - x_n) \end{cases} \quad (2)$$

In basic dual algorithm formula (2), F* denotes an adjoint function of function F, x denotes the magnetic-resonance image to be reconstructed, d denotes a dual parameter, prox denotes an approximate mapping function, σ, τ and θ are free parameters, n denotes a positive integer greater than or equal to 0, and $P_n$ denotes a connection factor for a dual iteration and a basic iteration. However, in the above iterative algorithm, the solving operator and the parameter structure relationship are all set manually, so accuracy of the iterative algorithm cannot be guaranteed.

In this embodiment, the above basic dual algorithm is improved, and one or more of a solving operator, a free parameter and a structural relationship in the iterative algorithm are learned in the mode of the magnetic-resonance imaging model, so that the freedom degree of the magnetic-resonance imaging model is improved; and the magnetic-resonance imaging model is trained on the basis of the sample data, so that the imaging precision of the magnetic-resonance imaging model is improved and the quality of the magnetic-resonance imaging is improved. In an embodiment, the fixed solving operator, free parameter and structural relationship of formula (2) are replaced on the basis of the undetermined solving operator, free parameter and structural relationship, and the above undetermined factors are learned through the magnetic-resonance imaging model. Exemplarily, references can be made to basic dual algorithm formula (3) and basic dual algorithm formula (4).

$$\begin{cases} d_{n+1} = \Gamma(d_n + \sigma A p_n, y) \\ x_{n+1} = \Lambda(x_n - \tau A^* d_{n+1}) \\ p_{n+1} = x_{n+1} + \theta(x_{n+1} - x_n) \end{cases} \quad (3)$$

$$\begin{cases} d_{n+1} = \Gamma(d_n, A x_n, y) \\ x_{n+1} = \Lambda(x_n, A^* d_{n+1}) \end{cases} \quad (4)$$

In the above basic dual algorithm formula (3) or basic dual algorithm formula (4), Γ denotes an undetermined dual iteration function; Λ denotes an undetermined basic iteration function, where corresponding functions of Γ and Λ may be different in formula (3) or formula (4); $A = F_u$; A* denotes an adjoint function of function A; σ, τ and θ are undetermined parameters; and $P_n$ denotes the connection factor for the dual iteration and the basic iteration. The above basic dual algorithm formula (3) or basic dual algorithm formula (4) is only an implementation mode, and the undetermined factors of the algorithm may be set according to user needs to form a corresponding iterative algorithm, which is not limited.

In an embodiment, the iterative algorithm is selected according to the number of samples and a precision requirement of the magnetic-resonance imaging model. Since basic dual algorithm formula (3) includes the undetermined solving operator and the undetermined parameter and basic dual algorithm formula (4) includes the undetermined solving operator, the undetermined parameter and the undetermined structure relationship, the number of samples required in the training process for the magnetic-resonance imaging model established on the basis of basic dual algorithm formula (3) is smaller than the number of samples required in the training process for the magnetic-resonance imaging model established on the basis of dual algorithm formula (4). Accordingly, the a precision requirement of the magnetic-resonance imaging model established and obtained through the training of the basis of basic dual algorithm formula (3) is lower than the a precision requirement of the magnetic-resonance imaging model established and obtained through the training of the basis of basic dual algorithm formula (4).

Figure 3:
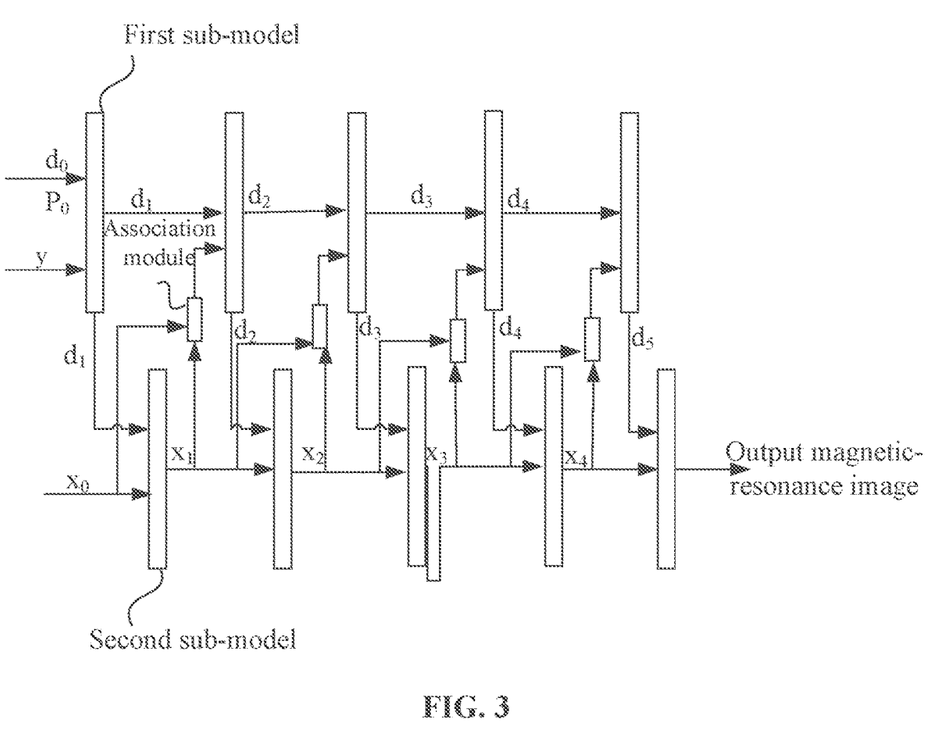
FIG. 3 is a schematic diagram of an initial imaging model according to embodiment one of the present application.

Exemplarily, the step in which the initial imaging model is established on the basis of basic dual algorithm formula (3) may include that: at least one first sub-model for performing the dual iteration is established, at least one second sub-model for performing the basic iteration is established, and an association module of the first sub-model and the second sub-model is determined according to an association relationship between the dual iteration and the basic iteration; a connection relationship between the first sub-model, the second sub-model and the association module is determined according to an iteration relationship between the dual iteration and the basic iteration; and the at least one first sub-model, the at least one second sub-model and the association module are connected according to the connection relationship to generate the initial imaging model. In this embodiment, the initial imaging model established on the basis of basic dual algorithm formula (3) includes preset layers of first sub models and second sub models. The preset layers of first sub models and the second sub models may both be a network model including multiple network layers. Referring FIG. 3, FIG. 3 is a schematic diagram of the initial imaging model according to embodiment one of the present application. In FIG. 3, each first sub-model receives output information of a first sub-model for a previous layer and output information of a second sub-model processed by an association module of the previous layer, processes the received information on the basis of a first undetermined parameter, and then input the processed information into a network layer of the each first sub-model; each second sub-model is used to receive an output result of a first sub-model for the same layer and an output result of a second sub-model for the previous layer, process the received information on the basis of a second undetermined parameter, and then input the processed information into a network layer of the each second sub-model; and the association module is used to process output information of the each second sub-network module and output information of a previous sub-network module on the basis of a third undetermined parameter, and then send the processed result to a first sub-model for a next layer. In this embodiment, a first sub-model and a second sub-model for each layer perform iteration reconstruction on the input information to generate the magnetic-resonance image. A first sub-model and a second sub-model for the first layer are used for receiving initial input information of the magnetic-resonance imaging model.

Figure 4:
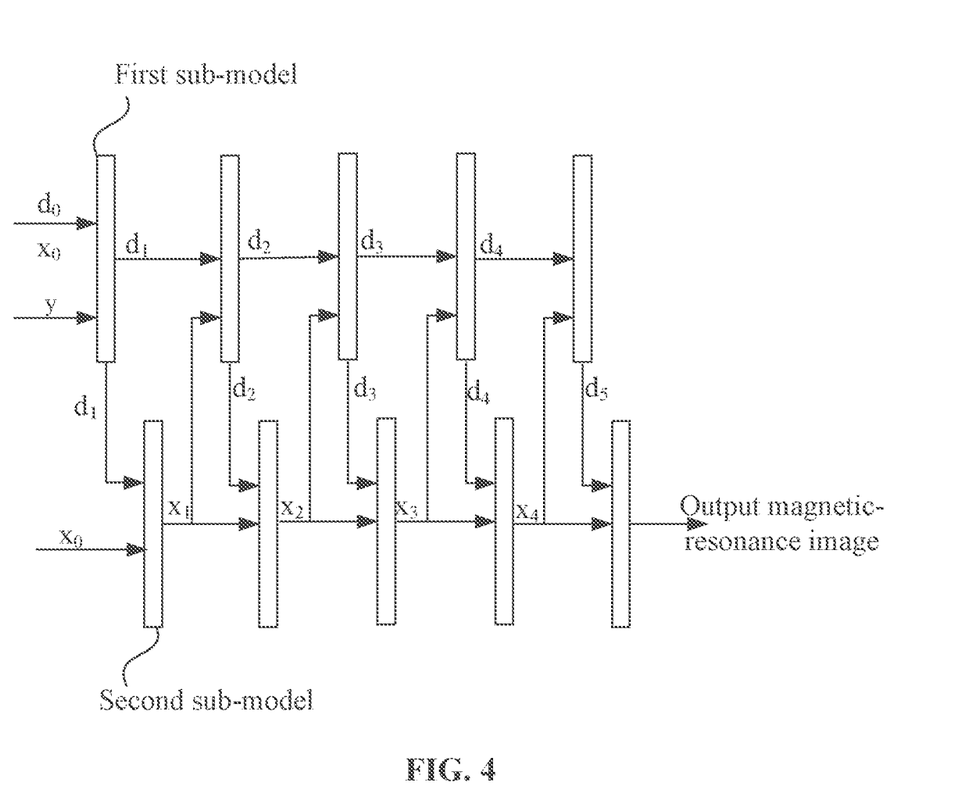
FIG. 4 is a schematic diagram of another initial imaging model according to embodiment one of the present application.
Figure 5:
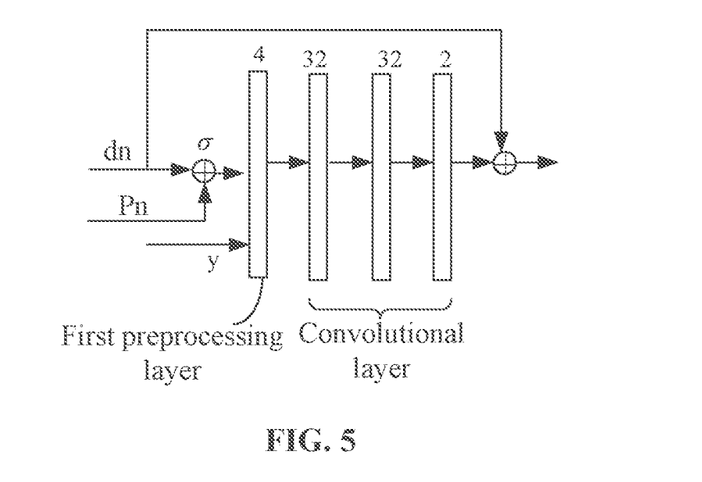
FIG. 5 is a schematic diagram of a first sub-model of an initial imaging model established on the basis of basic dual algorithm formula (3) according to embodiment one of the present application.

Exemplarily, the step in which the initial imaging model is established on the basis of basic dual algorithm formula (4) may include that: at least one first sub-model for performing the dual iteration is established, at least one second sub-model for performing the basic iteration is established; a connection relationship between the first sub-model and the second sub-model is determined according to the iteration relationship between the dual iteration and the basic iteration; and the at least one first sub-model and the at least one second sub-model are connected according to the connection relationship to generate the initial imaging model. The initial imaging model, established on the basis of basic dual algorithm formula (4), includes first sub models and second sub models in preset layers. An output end of each first sub-model is separately connected to an input end of a second sub-model for the same layer and an input end of a first sub-model for a next layer, and an output end of each second sub-model is separately connected to an input end of a first sub-model and an input end of a second sub-model for a next layer. Referring to FIG. 4, FIG. 4 is a schematic diagram of another initial imaging model according to embodiment one of the present application.

In this embodiment, the preset layers of the initial imaging model may be determined according to the number of iterations, exemplarily, the preset layers may be, but are not limited to, 10 layers or 15 layers, and may be determined according to the precision requirement of the magnetic-resonance image. The higher the precision of the magnetic-resonance image is, the more the layers of the initial imaging model are. FIGS. 3 and 4 are only schematic diagrams of the initial imaging model. In other embodiments, the layers of the initial imaging model may be set according to the user needs. In an embodiment, before an initial neural network is established, the number of layers input by a user may be received; or the precision requirement of the magnetic-resonance image input by the user is received, and the number of layers is determined according to the precision requirement of the magnetic-resonance image.

In this embodiment, basic dual algorithm formula (3) and basic dual algorithm formula (4) each includes the dual iteration and the basic iteration, and accordingly, initial imaging models each includes the first sub-model and the second sub-model. The initial imaging models may be network models. Accordingly, the first sub-model and the second sub-model are both sub-network models, and each may be formed by at least one convolution layer, activation function layer, pooling layer and the like. Exemplarily, both the first sub-model and the second sub-model may include a preset number of convolution layers used for performing convolution processing on the input information.

In an embodiment, the first sub-model is a first residual-error network. In the neural network, the depth of the network is an important factor influencing the effect, and the greater the depth of the network is, the higher the level of extracted feature information is, thereby helping improve precision of the output result. However, the problem of gradient diffusion/explosion is easy to occur along with an increase of the depth of the neural network, so that the neural network cannot be converged. The residual-error network is used for increasing the depth of the neural network without changing expression ability and complexity of the network, and for improving an output precision of the neural network. In an embodiment, a front end and a tail end of the first residual-error network are subjected to jump connection, so that the input and the output of each residual-error block are directly connected. This helps extract and retain image detail features, thereby improving a convergence speed of a training process of the neural network. In an embodiment, the first residual-error network includes a convolutional layer and an activation layer. The number of convolutional layers may be 3. The activation layer is disposed between two adjacent convolutional layers, and the convolution kernel of the convolutional layer may be 3×3. Exemplarily, in one embodiment, the numbers of output channels of the three convolutional layers of the first residual network are 32, 32 and 2 in sequence. In an embodiment, the first sub-model further includes a first preprocessing layer. The first preprocessing layer is connected to the first residual-error network and is used for preprocessing, according to a preset rule, different types of input parameters received by the first sub-model, and sending generated first multidimensional matrix data to the first residual-error network. Since a structural relationship between multiple pieces of input data needs to be learned, the first preprocessing layer is used for preprocessing the received multiple pieces of data. In an embodiment, the preprocessing may be stacking the received multiple pieces of data. In an embodiment, the preprocessing may be generating, according to a preset rule, the first multidimensional matrix from the received multiple pieces of data, and sending the generated first multidimensional matrix data to the convolutional layer of the first residual error network for the convolution processing. In an embodiment, the number of channels of the first preprocessing layer is determined on the basis of input information of the first sub-network module. In an embodiment, the number of channels of the first preprocessing layer may be twice the number of types of input information, and the channels are used for processing real-part data and imaginary-part data of the input information. For example, in this embodiment, the number of channels of the first preprocessing layer may be 4.

In an embodiment, the second sub-model includes a second residual-error network and a second preprocessing layer. The second preprocessing layer is connected to the second residual-error network and used for preprocessing, according to a preset rule, different types of input parameters received by the second sub-model, and sending generated second multidimensional matrix data to the second residual-error network. A front end and a tail end of the second residual-error network are subjected to jump connection. The second sub-model includes a convolutional layer and an activation layer. The convolution kernel of the convolutional layer is 3×3. Exemplarily, in one embodiment, the numbers of output channels of the three convolutional layers of the first residual network are 32, 32 and 2 in sequence. The second preprocessing layer preprocesses the received input data, for example, the preprocessing may be stacking the data, and generates a second multidimensional matrix. In this embodiment, the number of channels of the second preprocessing layer is determined on the basis of input information of the second sub-network module, for example, the number of channels of the second preprocessing layer may be 2, which is not repeated.

Figure 6:
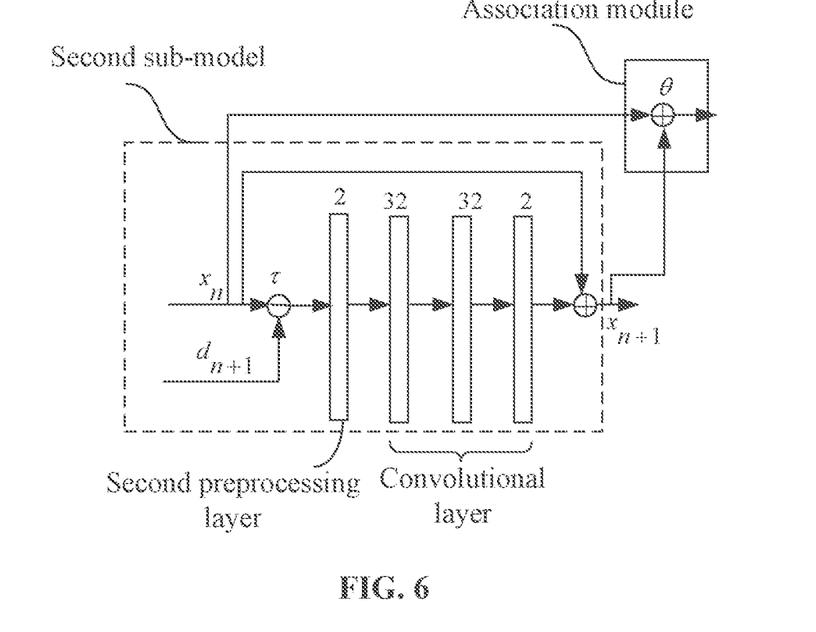
FIG. 6 is a schematic diagram of an association module and a second sub-model of an initial imaging model established on the basis of basic dual algorithm formula (3) according to embodiment one of the present application.
Figure 7:
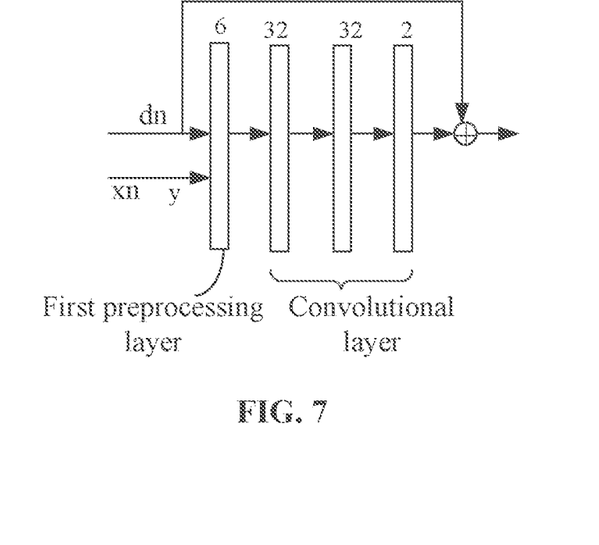
FIG. 7 is a schematic diagram of a first sub-model of an initial imaging model established on the basis of basic dual algorithm formula (4) according to embodiment one of the present application.
Figure 8:
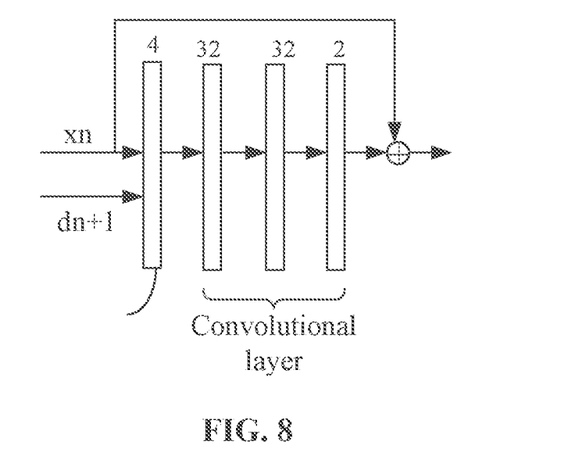
FIG. 8 is a schematic diagram of a second sub-model of an initial imaging model established on the basis of basic dual algorithm formula (4) according to embodiment one of the present application.

Exemplarily, referring FIGS. 5 to 8, FIG. 5 is a schematic diagram of a first sub-model of an initial imaging model established on the basis of basic dual algorithm formula (3) according to embodiment one of the present application, FIG. 6 is a schematic diagram of an association module and a second sub-model of an initial imaging model established on the basis of basic dual algorithm formula (3) according to embodiment one of the present application, FIG. 7 is a schematic diagram of a first sub-model of an initial imaging model established on the basis of basic dual algorithm formula (4) according to embodiment one of the present application, and FIG. 8 is a schematic diagram of a second sub-model of an initial imaging model established on the basis of basic dual algorithm formula (4) according to embodiment one of the present application.

In an embodiment, each convolutional layer of the first residual-error network and the second residual-error network includes a real-part channel and an imaginary-part channel. The real-part channel is used for performing the convolution processing on real-part data of input information of the convolutional layer, and the imaginary-part channel is used for performing the convolution processing on imaginary-part data of the input information of the convolutional layer. Since a magnetic-resonance signal is a complex signal and the neural network model cannot directly process the complex data, the magnetic-resonance signal is represented as real-part data and imaginary-part data. On the basis of features of the magnetic-resonance signal, the each convolutional layer of the first residual-error network and the second residual-error network includes the real-part channel and the imaginary-part channel. In an embodiment, the first preprocessing layer and the second preprocessing layer may also extract the real-part data and the imaginary-part data of the magnetic-resonance signal of the input information after receiving the input information, and preprocess the real-part data and the imaginary-part data separately. Accordingly, an output result of the real-part channel and an output result of the imaginary-part channel are combined so that an output magnetic-resonance image of the magnetic-resonance imaging model is determined.

Embodiment Two

Figure 9:
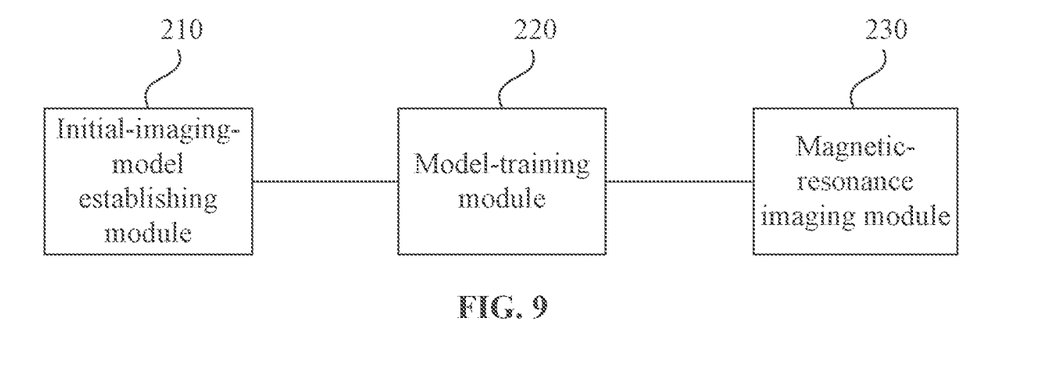
FIG. 9 is a structural diagram of a magnetic-resonance imaging apparatus according to embodiment two of the present application.

FIG. 9 is a structural diagram of a magnetic-resonance imaging apparatus according to embodiment two of the present application. The magnetic-resonance imaging apparatus includes an initial-imaging-model establishing module 210, a model-training module 220 and a magnetic-resonance imaging module 230.

The initial-imaging-model establishing module 210 is configured to acquire an original model for magnetic-resonance imaging and establish an initial imaging model according to an iterative algorithm used for solving the original model. The iterative algorithm includes at least one of an undetermined parameter, an undetermined solving operator or an undetermined structural relationship.

The model-training module 220 is configured to train the initial imaging model on the basis of sample data and generate a magnetic-resonance imaging model. Training of the initial imaging model is used for learning the at least one of the undetermined parameter, the undetermined solving operator or the undetermined structural relationship in the iterative algorithm.

The magnetic-resonance imaging module 230 is configured to acquire under-sampled K-space data to be processed, input the under-sampled K-space data into the magnetic-resonance imaging model, and generate a magnetic-resonance image.

In an embodiment, the model-training module 220 includes a first input-information determination unit and a first magnetic-resonance imaging-model generating unit.

The first input-information determination unit is configured to process first sample data in a sample set, an initial dual parameter and an initial image on the basis of the undetermined parameter and a preset structural relationship to obtain first input information.

The first magnetic-resonance imaging-model generating unit is configured to iteratively train the initial imaging model on the basis of the first input information, learn the undetermined parameter, and generate a first magnetic-resonance imaging model used for the magnetic-resonance imaging. The initial imaging model includes a preset number of iteration modules, the preset number of iteration modules are sequentially connected and used for iteratively processing the first input information, and each iteration module includes a preset solving operator.

In an embodiment, the model-training module 220 includes a second input-information determination unit and a second magnetic-resonance imaging-model generating unit.

The second input-information determination unit is configured to process second sample data in the sample set, the initial dual parameter and the initial image on the basis of the undetermined parameter and the preset structural relationship to obtain second input information.

The second magnetic-resonance imaging-model generating unit is configured to iteratively train the initial imaging model on the basis of the second input information, learn the undetermined parameter and a network parameter of the initial imaging model, and generate a second magnetic-resonance imaging model used for the magnetic-resonance imaging. The initial imaging model includes a preset number of iteration sub-network models, the preset number of iteration sub-network models are sequentially connected and used for iteratively processing the second input information, and the network parameter of the initial imaging model is used for replacing the preset solving operator.

In an embodiment, the model-training module 220 further includes a third input-information determination unit and a third magnetic-resonance imaging-model generating unit.

The third input-information determination unit is configured to use unprocessed third sample data in the sample set, the dual initial parameter and the initial image as third input information after the second magnetic-resonance imaging model used for the magnetic-resonance imaging is generated.

The third magnetic-resonance imaging-model generating unit is configured to train the second magnetic-resonance imaging model on the basis of the third input information, learn the undetermined structural relationship and the undetermined solving operator, and generate a third magnetic-resonance imaging model used for the magnetic-resonance imaging.

In an embodiment, in the case where the original model for the magnetic-resonance imaging includes a sparse transform algorithm, the apparatus further includes a sub-network establishing module and a fourth magnetic-resonance imaging-model generating module.

The sub-network establishing module is configured to establish a sub-network model for executing the sparse transform algorithm. The sub-network model is connected to an output end of the magnetic-resonance imaging model.

The fourth magnetic-resonance imaging-model generating module is configured to train the sub-network model on the basis of fourth sample data in the sample set, and generate a fourth magnetic-resonance imaging model on the basis of the trained sub-network model.

In an embodiment, the model-training module 220 includes a loss-function determination unit and a magnetic-resonance imaging-model adjusting unit.

The loss-function determination unit is configured to input the sample data into the initial imaging model to obtain an output magnetic-resonance image of the initial imaging model, and determine a loss function according to the output magnetic-resonance image and a standard magnetic-resonance image generated through full-sampled K-space data corresponding to the sample data. The loss function loss has calculation formula described below.

loss=$\|\hat{x}-x_{ref}\|_2^2$, where $\hat{x}$ denotes the output magnetic-resonance image of the initial imaging model and $x_{ref}$ denotes the standard magnetic-resonance image generated through the full-sampled K-space data corresponding to the sample data.

The magnetic-resonance imaging-model adjusting unit is configured to adjust the network parameter of the initial imaging model according to the loss function, and generate the magnetic-resonance imaging model.

In an embodiment, the iterative algorithm includes one of a basic dual algorithm, an alternating direction multiplier algorithm or an iterative threshold shrinkage algorithm.

The magnetic-resonance imaging apparatus provided by the embodiment of the present application can perform the magnetic-resonance imaging method provided by any embodiment of the present application, and has corresponding functional modules and beneficial effects for executing the magnetic-resonance imaging method.

Embodiment Three

Figure 10:
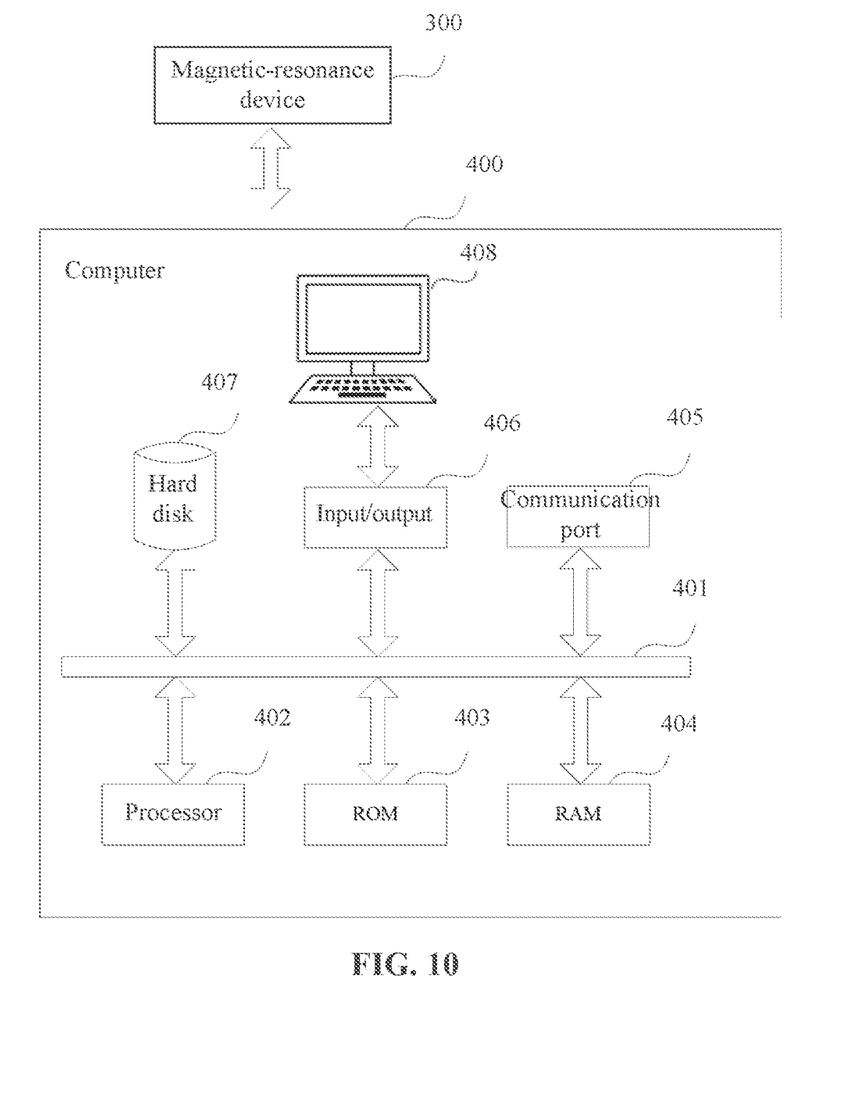
FIG. 10 is a structural diagram of a magnetic-resonance system according to embodiment three of the present application.

FIG. 10 is a structural diagram of a magnetic-resonance system according to embodiment three of the present application. FIG. 10 shows a block diagram of an exemplary medical-imaging system applicable in implementing embodiments of the present application. The medical-imaging system shown in FIG. 10 is only an example and not intended to limit the functions and the usable range of the embodiments of the present application.

The magnetic-resonance system includes a magnetic-resonance device 300 and a computer 400.

The computer 400 may be used for implementing a specific method and apparatus disclosed in some embodiments of the present application. The specific apparatus in this embodiment is illustrated by a functional block diagram of a hardware platform including a display module. In some embodiments, the computer 400 may implement some embodiments of the present application through hardware devices, software programs, firmware of the computer 400, and combinations thereof. In some embodiments, the computer 400 may be a general-purpose computer, or a specific-purpose computer.

As shown in FIG. 10, the computer 400 may include an internal communication bus 401, a processor 402, a read-only memory (ROM) 403, a random access memory (RAM) 404, a communication port 405, an input/output component 406, a hard disk 407 and a user interface 408. The internal communication bus 401 may implement data communication between components of the computer 400. The processor 402 may make determination and issue prompts. In some embodiments, the processor 402 may be composed of one or more processors. The communication port 405 may implement data communication between the computer 400 and other components (not shown in FIG. 10), such as an external device, an image-acquisition device, a database, an external storage, an image-processing workstation and the like. In some embodiments, the computer 400 may send and receive information and data via a network through the communication port 405. The input/output component 406 support input/output data flows between the computer 400 and other components. The user interface 408 may implement interaction and information exchange between the computer 400 and a user. The computer 400 may further include various forms of program storage units and data storage units, such as the hard disk 407, the ROM 403 and the RAM 404, can store one or more data files used for computer processing and/or communication, and can store possible program instructions executable for the processor 402.

The processor may be used for performing a magnetic-resonance imaging method when executing the programs. The method includes acquiring an original model for magnetic-resonance imaging and establishing an initial imaging model according to an iterative algorithm used for solving the original model, where the iterative algorithm includes at least one of an undetermined parameter, an undetermined solving operator or an undetermined structural relationship; training the initial imaging model on the basis of sample data and generating a magnetic-resonance imaging model, where training of the initial imaging model is used for learning the at least one of the undetermined parameter, the undetermined solving operator or the undetermined structural relationship in the iterative algorithm; and acquiring undersampled K-space data to be processed, inputting the under-sampled K-space data into the magnetic-resonance imaging model, and generating a magnetic-resonance image.

The present application uses specific words to describe embodiments of the present application. For example, "one embodiment", "an embodiment" and/or "some embodiments" means certain feature, structure or characteristic related to at least one embodiment of the present application. Therefore, it is to be emphasized and appreciated that "an embodiment" or "one embodiment" or "an alternative embodiment" twice or more-times mentioned in different positions of this specification are not necessarily all referring to a same embodiment. Furthermore, certain features, structures or characteristics of one or more embodiments of the present application may be appropriately combined.

Each aspect of the present application may be illustrated and described in terms of multiple species or situations including any new and useful combination of processes, machines, products or substances, or any new and useful improvement thereof. Accordingly, multiple aspects of the present application may be implemented entirely by hardware, entirely by software (including firmware, resident software, micro-code, etc.) or by a combination of hardware and software. The above hardware or software may be referred to as a "data block", "module", "sub-module", "engine", "unit", "sub-unit", "component" or "system". Furthermore, multiple aspects of the present application may be represented as computer products positioned in one or more computer-readable mediums. The computer products include computer-readable program codes.

Embodiment Four

Embodiment four of the present application provides a computer-readable storage medium storing a computer program. When the computer program is executed by a processor, the magnetic-resonance imaging method provided by any embodiment of the present application is performed. The method includes acquiring an original model for magnetic-resonance imaging and establishing an initial imaging model according to an iterative algorithm used for solving the original model, where the iterative algorithm includes at least one of an undetermined parameter, an undetermined solving operator or an undetermined structural relationship; training the initial imaging model on the basis of sample data and generating a magnetic-resonance imaging model, where training of the initial imaging model is used for learning the at least one of the undetermined parameter, the undetermined solving operator or the undetermined structural relationship in the iterative algorithm; and acquiring under-sampled K-space data to be processed, inputting the under-sampled K-space data into the magnetic-resonance imaging model, and generating a magnetic-resonance image.

The computer-readable signal medium may include a propagated data signal with computer program codes therein, for example, on a baseband or as part of a carrier wave. The propagated signal may take multiple forms including an electromagnetic form, an optical form and the like, or any appropriate combination. The computer-readable signal medium may be any computer-readable medium excluding a computer-readable storage medium. The medium may be connected to an instruction execution system, apparatus or device to communicate, propagate, or transmit a program for use. The program codes on the computer-readable signal medium may be propagated over any appropriate medium including radio, an electrical cable, a fiber cable, radio-frequency signals or the like, or any combination of the preceding mediums.

The computer program codes required for operations of multiple parts of the present application may be written in any one or more programming languages including an object-oriented programming language such as Java, Scala, Smalltalk, Eiffel, JADE, Emerald, C++, C#, VB.NET, Python and the like; a conventional programming language such as C, Visual Basic, Fortran 2003, Perl, COBOL 2002, PHP and ABAP; a dynamic programming language such as Python, Ruby and Groovy; or other programming languages. The program codes may run entirely on a user computer, or run on the user computer as an independent software package, or run partly on the user computer and partly on a remote computer, or run entirely on the remote computer or server. In the latter case, the remote computer may be connected to the user computer via any network format, such as a local area network (LAN) or a wide area network (WAN); or be connected to an external computer (for example, via Internet); or be used as a service, for example, software as a service (SaaS), in cloud-computing environment.

Furthermore, the order in which elements and sequences are processed, the use of alphanumeric characters, or the use of other designations is not intended to limit the order of processes and methods of the present application, unless explicitly claimed. Although some useful embodiments have been discussed herein through various examples, such details are only for illustrative purposes, and appended claims are not limited to the disclosed embodiments. For example, although the system components described above may be implemented by hardware devices, the system components may be implemented by software-only solutions, for example, installing the described system on a server or mobile device.

To simplify description disclosed in the present application and thereby help understanding of one or more embodiments of the present application, the foregoing description of the embodiments of the present application sometimes incorporate multiple features into one embodiment, drawing or description thereof. However, this disclosure method is not intended to imply that objects of the present application require more features than objects mentioned in the claims. In fact, the number of features of the embodiments is less than the number of all features of the single embodiment disclosed above.

Some embodiments use a number to describe components and attributes, or such number used in description of the embodiments. The number is modified in some examples by using modifier "about", "approximately" or "substantially". Unless otherwise indicated, "about", "approximately" or "substantially" indicates that the number allows a variation of ±20%. Accordingly, in some embodiments, numerical parameters used in the specification and claims are approximations. The approximations may vary according to desired characteristics of individual embodiments. In some embodiments, the numerical parameters should take into account specified significant digits and adopt a general-digit preserving method. Although numerical ranges and parameters used for confirming broad scope of some embodiment are approximations in the present application, such numerical values are set as precisely as possible within applicable scope in specific embodiments.

What is claimed is:

1. A magnetic-resonance imaging method, comprising:
   acquiring an original model for magnetic-resonance imaging and establishing an initial imaging model according to an iterative algorithm used for solving the original model, wherein the iterative algorithm comprises undetermined parameters, undetermined solving operators, and undetermined structural relationships, wherein the undetermined structural relationships are calculation relationships between multiple pieces of input information or between multiple pieces of input information processed through the undetermined parameter in the iterative algorithm;
   training the initial imaging model on a basis of sample data to generate a magnetic-resonance imaging model, wherein training of the initial imaging model is used for learning the undetermined parameters, the undetermined solving operators and the undetermined structural relationships in the iterative algorithm; and
   acquiring under-sampled K-space data to be processed, inputting the under-sampled K-space data into the magnetic-resonance imaging model, and generating a magnetic-resonance image.

2. The method of claim 1, wherein training the initial imaging model on the basis of the sample data and generating the magnetic-resonance imaging model comprises:
   processing first sample data in a sample set, an initial parameter and an initial image on a basis of the undetermined parameters and a preset structural relationship to obtain first input information; and
   iteratively training the initial imaging model on the basis of the first input information, learning the undetermined parameters, and generating a first magnetic-resonance imaging model used for the magnetic-resonance imaging;
   wherein the initial imaging model comprises a preset number of iteration modules, the preset number of iteration modules are sequentially connected and used for iteratively processing the first input information, and each of the iteration modules comprises a preset solving operator.

3. The method of claim 1, wherein training the initial imaging model on the basis of the sample data and generating the magnetic-resonance imaging model comprises:
   processing second sample data in a sample set, an initial parameter and an initial image on a basis of the undetermined parameters and a preset structural relationship to obtain second input information; and iteratively training the initial imaging model on the basis of the second input information, determining the undetermined parameters and a network parameter of the initial imaging model, and generating a second magnetic-resonance imaging model used for the magnetic-resonance imaging;

wherein the initial imaging model comprises a preset number of iteration sub-network models, the preset number of iteration sub-network models are sequentially connected and used for iteratively processing the second input information, and the network parameter of the initial imaging model is used for replacing a preset solving operator.

4. The method of claim 3, after generating the second magnetic-resonance imaging model used for the magnetic-resonance imaging, the method further comprising: using unprocessed third sample data in the sample set, the initial parameter and the initial image as third input information; and training the second magnetic-resonance imaging model on the basis of the third input information, learning the undetermined structural relationships and the undetermined solving operators, and generating a third magnetic-resonance imaging model used for the magnetic-resonance imaging.

5. The method of claim 1, in a case where the original model for the magnetic-resonance imaging comprises a sparse transform algorithm, the method further comprising:

establishing a sub-network model for executing the sparse transform algorithm, wherein the sub-network model is connected to an output end of the magnetic-resonance imaging model; and training the sub-network model on a basis of fourth sample data in the sample set and generating a fourth magnetic-resonance imaging model on a basis of the trained sub-network model.

6. The method of claim 1, wherein training the initial imaging model on the basis of the sample data and generating the magnetic-resonance imaging model comprises:

inputting the sample data into the initial imaging model to obtain an output magnetic-resonance image of the initial imaging model, and determining a loss function according to the output magnetic-resonance image and a standard magnetic-resonance image generated through full-sampled K-space data corresponding to the sample data, and adjusting a network parameter of the initial imaging model according to the loss function and generating the magnetic-resonance imaging model wherein the loss function loss is calculated using the following calculation formula:

loss=$\|\hat{x} - x_{ref}\|_2^2$, wherein $\hat{x}$ denotes the output magnetic-resonance image of the initial imaging model and $x_{ref}$ denotes the standard magnetic-resonance image generated through the full-sampled K-space data corresponding to the sample data.

7. The method of claim 1, wherein the iterative algorithm comprises one of a basic dual algorithm, an alternating direction multiplier algorithm or an iterative threshold shrinkage algorithm.

8. A non-transitory computer-readable storage medium, storing a computer program, wherein when the computer program is executed by a processor, the magnetic-resonance imaging method of claim 1 is performed.

9. A magnetic-resonance imaging system, comprising a magnetic-resonance device and a computer device, wherein the computer device comprises a memory, at least one processor and a computer program stored in the memory and executable on the processor, and the processor is capable of performing the magnetic-resonance imaging method of claim 1 when the processor executes the computer program.

10. The method of claim 1, wherein a formula of the iterative algorithm is $$\begin{cases} d_{n+1} = \Gamma(d_n, Ax_n, y) \\ x_{n+1} = \Lambda(x_n, A^* d_{n+1}) \end{cases}$$

wherein d denotes a dual parameter, n denotes a positive integer greater than or equal to 0, $\Gamma$ denotes an undetermined dual iteration function, $\Lambda$ denotes an undetermined basic iteration function, $A=F_u$ and $F_u$ denotes an under-sampled Fourier transform operator, $A^*$ denotes an adjoint function of function A, x denotes a magnetic-resonance image to be reconstructed, and y denotes under-sampled K-space data obtained through magnetic-resonance scanning.

11. A magnetic-resonance imaging apparatus, comprising at least one processor and a memory for storing a computer program that when executed by the processor causes the processor to perform steps in following modules:

an initial-imaging-model establishing module, which is configured to acquire an original model for magnetic-resonance imaging and establish an initial imaging model according to an iterative algorithm used for solving the original model, wherein the iterative algorithm comprises undetermined parameters, undetermined solving operators, or and undetermined structural relationships, wherein the undetermined structural relationships are calculation relationships between multiple pieces of input information or between multiple pieces of input information processed through the undetermined parameter in the iterative algorithm;

a model-training module, which is configured to train the initial imaging model on a basis of sample data to generate a magnetic-resonance imaging model, wherein training of the initial imaging model is used for learning the undetermined parameters, the undetermined solving operators, and the undetermined structural relationships in the iterative algorithm; and a magnetic-resonance imaging module, which is configured to acquire under-sampled K-space data to be processed, input the under-sampled K-space data into the magnetic-resonance imaging model, and generate a magnetic-resonance image.

* * * * *